United States Patent [19]
Bergfeld et al.

[11] Patent Number: 5,977,350
[45] Date of Patent: Nov. 2, 1999

[54] PROCESS FOR THE OXIDATION OF DI-, TRI-, OLIGO- AND POLYSACCHARIDES INTO POLYHYDROXYCARBOXYLIC ACIDS

[75] Inventors: Manfred Bergfeld, Erlenbach; Ludwig Eisenhuth, Obernburg, both of Germany

[73] Assignee: Akzo Nobel N.V.

[21] Appl. No.: 09/149,743

[22] Filed: Sep. 8, 1998

Related U.S. Application Data

[63] Continuation of application No. PCT/EP97/01435, Mar. 19, 1997.

[30] Foreign Application Priority Data

Mar. 21, 1996 [EP] European Pat. Off. ............. 96200786

[51] Int. Cl.⁶ ........................... C07O 17/00; C13K 13/00
[52] U.S. Cl. ................. 536/124; 536/123.1; 536/123.13
[58] Field of Search .............................................. 536/124

[56] References Cited

U.S. PATENT DOCUMENTS 4,985,553  1/1991  Fuertes et al. .......................... 536/124

FOREIGN PATENT DOCUMENTS 151498  8/1985  European Pat. Off. ........ C07H 7/027

OTHER PUBLICATIONS

H.E.J. Hendriks et al., "The Effect of Bismuth on the Selective Oxidation of Lactose on Supported Palladium Catalysts", Carbohydrate Research, 204 (1990), pp. 121–129.

Derwent Patent Abstract No. 68340/B (1979).

Derwent Patent Abstract No. 89–316885/44 (1989).

*Primary Examiner*—Gary Geist
*Assistant Examiner*—Robert W. Deemie
*Attorney, Agent, or Firm*—Richard P. Fennelly

[57] ABSTRACT

A process is provided for preparing polyhydroxycarboxylic acids by the selective oxidation of di-, tri-, oligo- and polysaccharides in an alkaline medium using an oxygenous gas in the presence of palladium on a carrier as catalyst and bismuth as promoter at a palladium concentration in the reaction mixture of at least about 40 mg/l and a molar ratio of bismuth to palladium in the range of from about 1:5 to about 1:40, in which process towards the end of the reaction, as soon as a strong increase is observed in the oxygen concentration in the liquid phase, the oxygen supply is reduced until it is not more than about 20 ppm. In this manner, virtually all of the polysaccharide added beforehand is converted into the desired end product without an unacceptably high concentration of bismuth in the end product.

15 Claims, No Drawings

PROCESS FOR THE OXIDATION OF DI-, TRI-, OLIGO- AND POLYSACCHARIDES INTO POLYHYDROXYCARBOXYLIC ACIDS

The present application is a Continuation of International Patent Application No. PCT/EP97/01435, filed on Mar. 19, 1997.

BACKGROUND OF THE INVENTION

The invention relates to the preparation of polyhydroxycarboxylic acids by the selective oxidation of di-, tri-, oligo- and polysaccharides in an alkaline medium using an oxygenous gas in the presence of palladium on a carrier as catalyst and bismuth as promoter.

Such a process is known from U.S. Pat. No. 4,985,553, and a further working-out of the oxidation of lactose can be found in an article by H. Hendriks et al. in *Carbohydrate Research* 204 (1990), 121–129.

A drawback to the process described in said publications is that although the percentage of polysaccharides which can be converted in this manner is over 90%, notably in the oxidation of lactose it fails to advance beyond 95%. In Example V of the aforementioned patent publication a conversion rate of 91% is listed for the oxidation of lactose. Such a mixture of polysaccharide or aldose and salt of the corresponding carboxylic acid is hard to purify on a commercial scale. Moreover, the product was found to be too badly contaminated with residual catalyst. A further drawback to the process claimed in the U.S. patent is the laborious catalyst preparation. It involves mixing a solution of a bismuth compound, with vigorous stirring, with an aqueous suspension of the palladium deposited onto a carrier. The whole is made alkaline by adding a base, followed by reduction of the bismuth compound with formalin, sodium formate, sodium boron hydride, hypophosphorous acid, hydrazine, glucose, or other reducing sugars. The catalyst thus reduced is filtered, washed, and dried.

DESCRIPTION OF THE INVENTION

The invention now provides a process that largely obviates the aforementioned drawbacks. The invention relates to a process of the previously described type mentioned in which the reaction is carried out at a palladium concentration in the reaction mixture of at least 40 mg/l and a molar ratio of bismuth to palladium in the range of from about 1:5 to about 1:40, in which process towards the end of the reaction, as soon as a strong increase is observed in the oxygen concentration in the liquid phase, the oxygen supply is reduced until it is not more than about 20 ppm.

Surprisingly, it has been found that when before the end of the reaction a reduction of the supply of oxygen ensures that the oxygen concentration in the liquid phase cannot exceed about 20 ppm, the catalyst is hardly deactivated, if at all. In consequence, virtually all of the polysaccharide added beforehand is converted into the desired end product within a reasonable period of time. Deactivation of the catalyst leads to an unacceptably long reaction time and incomplete conversion of the starting material. For instance, in Example V of U.S. Pat. No. 4,985,553 after a reaction time of one hour and twenty minutes only 91% of the lactose has been converted.

To obtain a satisfactory result it is also essential to have a palladium concentration in the reaction mixture of at least about 40 mg/l and a molar ratio of bismuth to palladium that stays within the claimed range. A molar ratio of bismuth to palladium of above about 1:5 results in an unacceptably high concentration of bismuth in the end product and an increased reaction time. A molar ratio of bismuth to palladium of below about 1:40, on the other hand, produces incomplete conversion of the polysaccharide employed.

According to the present invention, preference is given to a process where before the end of the reaction a reduction of the supply of oxygen ensures that the oxygen concentration in the liquid phase does not exceed about 10 ppm. Optimum results are attained in this case when the reduction of the oxygen supply is adjusted such that the oxygen concentration in the liquid phase cannot exceed about 5 ppm, and preferably cannot exceed about 1 ppm.

Examples of polysaccharides which can be oxidized using the process according to the invention are lactose, maltose, isomaltose, cellobiose, xylobiose, and mannobiose. Optimum results so far have been attained using lactose and maltose.

Oxygen can be passed into the reaction mixture in many different ways. So far, favorable results have been attained dosing oxygen, air or nitrogen diluted oxygen at the start of the reaction. During the reaction the oxygen concentration in the liquid phase is continuously measured with a sensor. One way of adjusting the oxygen concentration in the liquid reaction mixture is by controlling the rate of stirring of the preferably employed turbo stirrer. The polysaccharide conversion is easily calculated from the amount of lye needing to be added to maintain a constant pH level. By varying the rate of stirring in the reaction mixture the oxygen concentration in the reaction mixture can be continuously adjusted, which adjustment can be refined further by greater dilution of the oxygenous gas with nitrogen.

A major advantage of the process now proposed is that the promoter need not first be incorporated into the catalyst via a laborious process, but can be added to the reaction mixture separately. As regards the palladium, advantageous use may be made of various commercially available embodiments where the palladium is deposited on a carrier of activated carbon. The bismuth may be added with advantage in the form of an aqueous solution of $Bi(NO_3)_3 \cdot 5H_2O$. Optimum results in that case are obtained with a palladium concentration of about 100 mg/l and a bismuth concentration of about 20 mg/l. Alternatively, the bismuth may be added in the form of $Bi_2O_3$.

One important advantage of the option of adding the bismuth separately is that complicated catalyst preparation may be dispensed with. A further advantage of the process according to the present invention is that there is no need to regenerate the catalyst after every cycle. For, surprisingly, it has been found that the catalyst can be re-used many times in a row without any noticeable loss of activity if, on conclusion of the reaction, the reaction mixture is heated for about 1 to about 30 minutes, preferably for about 5 to about 15 minutes at a temperature in the range of from about 50° to about 90° C., preferably in the range of from about 65° to about 85° C., prior to being filtered off at that temperature. The filtered catalyst is immediately ready for use in a new oxidation cycle, while the filtrate can be refined further, for example, by freeze-drying. If there is no heating at the end of each oxidation cycle, a reaction time increasing with every cycle and an increased loss of palladium should be taken into account.

The temperature at which the reaction can be carried out to favorable effect ranges from about 20° to about 90° C., with preference being given to a temperature ranging from about 30° to about 70° C., optimum results so far having been attained at a temperature ranging from about 35° to about 55° C.

The reaction is commonly carried out in such a way that first the catalyst is added beforehand to an aqueous solution of a polysaccharide with a polysaccharide concentration of from about 5 to about 60 wt. %, followed by the introduction, with vigorous stirring, of an oxygenous gas and the simultaneous charging of an alkaline reacting substance to neutralize the formed carboxylic acid, the pH being kept at a value in the range of from about 7.5 to about 11, preferably in the range of from about 8 to about 10. The neutralizing agent used may be sodium hydroxide, potassium hydroxide, calcium hydroxide, lithium hydroxide, magnesium hydroxide, or a carbonate such as sodium carbonate, or else zinc or manganese carbonate, or an amine such as triethyl amine.

The invention will be further elucidated with reference to the following Examples, which are for illustrative purposes only and in no way seek to limit the scope of the invention.

EXAMPLE 1

In a 1 l glass reactor with a double jacket, equipped with a turbo stirrer, an oxygen sensor, and a pHstat, 5.52 g of Pd/C catalyst (5.2% of Pd, 63.7% of water, Johnson Matthey) and 57 mg of bismuth subnitrate pentahydrate were suspended in 100 g of water and added to a solution obtained by heating 92.9 g of α-lactose•$H_2O$ (97%, Aldrich, 0.25 mole) and 307 g of water.

The reaction was carried out at 40° C. in an air atmosphere at standard pressure, with the air from the gas phase of the reactor being contacted with the reaction mixture through vigorous stirring. At the same time, the pH was kept at 9 by the corresponding addition of 20% caustic soda. To keep the oxygen content in the gas phase at a constant level, an air stream was passed through the gas phase during the reaction. As soon as 98% of the theoretical amount of caustic soda had been used up, the oxygen concentration in the solution began to increase. For that reason the oxygen supply to the reaction mixture was reduced by lowering the rotational speed of the stirrer, such that the oxygen concentration remained below 1 ppm.

After seventy-six minutes, all of the computed caustic soda had been added, and the reaction came practically to a stop and was concluded. The reaction solution was separated from the catalyst by filtration and freeze-dried. Obtained from the reaction was 104.9 g of a white solid which, according to $^{13}C$ NMR analysis, consisted of substantially pure sodium lactobionate. The sodium lactobionate content was determined to be 98.5% (via ion exchange and titration of the free acid). By HPLC analysis, it was determined that 0.5% of lactose remained in the product, which corresponds to a conversion of 99.4%. Moreover, catalyst traces in the product were subjected to atomic absorption analysis: Bi<0.1 ppm; and Pd 0.3 ppm.

EXAMPLE 2

Example 1 was repeated, except that in the gas phase of the reactor, instead of air, pure oxygen was used, which was introduced via a gas burette at standard pressure in accordance with consumption. At an NaOH consumption of 90% of the calculated amount the oxygen supply of the gas phase in the reaction mixture was reduced by lowering the rotational speed of the stirrer, such that the oxygen concentration in the solution was kept below 1 ppm. The reaction was concluded after twenty-six minutes at a caustic soda addition of 100% of theory. Product analyses: sodium lactobionate (98.4% of theory); lactose 0.4%; Bi<0.1 ppm; and Pd 0.5 ppm.

EXAMPLE 3 (COMPARATIVE EXAMPLE)

The process of Example 2 was repeated, except that the rotational speed of the stirrer was not lowered at the end. After thirty minutes, the NaOH addition came to a stop at 92% of the theoretical amount. The product was contaminated with 9% of unconverted lactose.

EXAMPLE 4

The process of Example 1 was repeated, except that on conclusion of the reaction after seventy-six minutes, the rotational speed of the stirrer was lowered to 150 rpm, and the reaction mixture was heated for ten minutes at 80° C. Next, at the same temperature, the reaction solution was removed from the reactor through a filter candle. The catalyst staying behind in the reactor was then used straight-away for a second cycle. This only involved the addition of a solution obtained by heating 92.9 g of lactose and 400 g of water, and bringing the suspension to reaction with air as in Example 1. In this way eleven reaction cycles in succession were carried out with the same catalyst. In the eleventh cycle, at a caustic soda addition of 96% of theory (increase in the oxygen concentration to 1 ppm), the rotational speed of the stirrer was adjusted, such that the oxygen concentration in the reaction mixture was kept below 1 ppm. After seventy-nine minutes, 100% of the calculated amount of caustic soda had been added, the reaction came practically to a stop, and was concluded.

The products from the eleven cycles were each freeze-dried and analyzed. All contained >98% sodium lactobionate and 0.1 ppm Bi as well as <0.05 ppm Pd.

EXAMPLE 5

The process of Example 4 was repeated, except that the reaction mixture was not subjected to further heating after the reaction but immediately was filtered through the filter candle at 40° C. In this way, ten reaction cycles were carried out, with the reaction time increasing with each cycle. In the tenth cycle, the oxygen concentration rose to 1 ppm at a caustic soda consumption of 87% and was adjusted by means of the turbo stirrer. The reaction time during this cycle was ninety-four minutes as compared with seventy-six minutes for the first cycle.

A further reaction cycle was performed with, in contrast to the first ten cycles, an additional 15 mg of bismuth subnitrate being added. In this process step, the oxygen concentration rose to 1 ppm at a caustic soda consumption of 98% of theory, and the rotational speed of the stirrer was lowered accordingly. The reaction period until 100% caustic soda consumption had been reached was seventy-eight minutes. The products of all reaction cycles had a sodium lactobionate content >98%, the lactose content was <0.6%, and the metal concentration was <0.1 ppm for Bi and 0.1–1 ppm for Pd.

EXAMPLE 6

(Comparative Example with a higher share of Bi, in accordance with "Carb. Res." 204 (1990), 121–129))

The process of Example 2 was carried out, except that this time only 1.38 g of the palladium was employed as the catalyst (the molar ratio of Pd:Bi was 1:1.9). Moreover, a reaction temperature of 50° C. was selected. The reaction did not start up until the reactor had been flushed with nitrogen repeatedly, followed by replacement of the nitrogen with oxygen. Once a caustic soda addition of 85% of theory had been reached, the oxygen concentration rose and was kept at <1 ppm by lowering the rotational speed of the stirrer. After forty-one minutes, the conversion was practically complete. The product in any case contained 62 ppm Bi and 0.2 ppm Pd.

EXAMPLE 7

As described in Example 2, instead of lactose, 90.1 g of a commercial starch hydrolysate ("Fermentose," 70% maltose, 20% maltotriose) was used. The reaction was carried out at 50° C. At a caustic soda addition of 210 mmoles, the oxygen concentration in the reaction mixture increased to 5 ppm and was kept at <5 ppm by lowering the rotational speed of the stirrer. After sixteen minutes, 225 mmoles of NaOH had been added, and the reaction came virtually to a stop. The reaction mixture was then heated at 80° C. for fifteen minutes with light stirring, after which, at the same temperature, the product solution was removed through a filter candle. By adding 90.1 g of fresh starch hydrolysate dissolved in 400 g of water immediately, a further cycle was carried out with the same catalyst, the reaction time now being eighteen minutes. A corresponding 3rd cycle lasted seventeen minutes. According to $^{13}$C NMR, the products contained, as the main component, sodium maltobionate. The metal concentration was <0,1 ppm for Bi and <1 ppm for Pd.

EXAMPLE 8

The process of Example 7 was carried out, except that heating of the reaction mixture to 80° C. at the end of the reaction was omitted. With this procedure the reaction time increased to thirty minutes in the second cycle and to seventy-five minutes in the third cycle. The catalyst activity was reduced very sharply.

EXAMPLE 9

The process of Example 2 was repeated, except that the reaction temperature was 50° C. and, instead of caustic soda, triethyl amine was used as base. The oxygen concentration was adjusted so as not to exceed a concentration of 4 ppm. After a reaction period of thirty minutes, the theoretical amount of triethyl amine had been added and the reaction came virtually to a stop. In this way, after the catalyst was filtered off, an aqueous solution of the triethyl ammonium salt of lactobionic acid was obtained (analysis by means of $^{13}$C NMR).

EXAMPLE 10

The process of Example 9 was repeated, except that, instead of triethyl amine, calcium hydroxide was added as base in the form of a 20% aqueous suspension. The oxygen concentration in this experiment was restricted to a maximum of 10 ppm. The reaction was complete after seventy minutes, and, after filtration and drying of the resulting solution, 99 g of calcium lactobionate was obtained as a beige-colored solid matter (analysis by means of $^{13}$C NMR).

EXAMPLE 11

The process of Example 2 was repeated, except that, instead of lactose, 0.25 mole of cellobiose was used. The reaction period was twenty minutes. In this way, the sodium salt of cellobionic acid was obtained. The conversion to a highly pure product was practically complete.

EXAMPLE 12

As described in Example 2, instead of lactose were used 100 g of a starch hydrolysate (composition: 5% glucose, 11% maltose, 14% triose, 8% tetrose, 10% pentose, 5% hexose, 25% heptose, 21% higher sugars), dissolved in 233 g water. The reaction was carried out at 50° C. At a caustic soda addition of 87 mmol, the oxygen concentration in the reaction mixture increased and was kept at <10 ppm by regulating the speed of the stirrer. After fifty minutes, 115 mmoles of NaOH had been added, and the reaction came virtually to a stop. The reaction mixture was then heated at 80° C. for fifteen minutes with light stirring, after which, at the same temperature, the product solution was removed through a filter candle. By adding 100 g of fresh starch hydrolysate dissolved in 233 g of water, a further cycle was carried out with the same catalyst, the reaction time now being also fifty-five minutes. According to $^{13}$C NMR, the products contained a mixture of polyhydroxycarboxylic acids, derived from the used oligosaccharides.

What is claimed is:

1. A process for preparing polyhydroxycarboxylic acids by the selective oxidation of di-, tri-, oligo- and polysaccharides in an alkaline medium using an oxygenous gas in the presence of palladium on a carrier as catalyst and bismuth as promoter, characterized in that at a palladium concentration in the reaction mixture of at least about 40 mg/l and a molar ratio of bismuth to palladium in the range of from about 1:5 to about 1:40, in which process towards the end of the reaction, as soon as a strong increase is observed in the oxygen concentration in the liquid phase, the oxygen supply is reduced until its concentration in the liquid phase is not more than about 20 ppm.

2. A process according to claim 1 wherein a reduction of the supply of oxygen ensures that the oxygen concentration in the liquid phase does not exceed about 10 ppm.

3. A process according to claim 1 wherein a reduction of the supply of oxygen ensures that the oxygen concentration in the liquid phase does not exceed about 5 ppm.

4. A process according to claim 1 wherein a reduction of the supply of oxygen ensures that the oxygen concentration in the liquid phase does not exceed about 1 ppm.

5. A process according to claim 1 wherein the polysaccharide is selected from the group consisting of maltose and lactose.

6. A process according to claim 1 wherein the oxygen supply in the reaction mixture is reduced by lowering the stirring speed of the agitator in the reactor.

7. A process according to claim 1 wherein the oxygen reduction in the reaction mixture is effected by diluting the oxygen gas passed into the reactor with an inert gas.

8. A process according to claim 1 wherein the bismuth is separately incorporated into the reaction mixture prior to the start of the reaction.

9. A process according to claim 1 wherein the palladium concentration is at least about 100 mg/l and the bismuth concentration is at least about 20 mg/l.

10. A process according to claim 1 wherein the reaction is carried out at a temperature in the range of from about 30° C. to about 70° C.

11. A process according to claim 10 wherein the reaction is carried out at a temperature in the range of from about 40° C. to about 55° C.

12. A process according to claim 1 wherein the bismuth is added in the form of a water-soluble salt.

13. A process according to claim 1 wherein the reaction is carried out at an initial polysaccharide concentration in the range of from about 10 to about 55 wt. %.

14. A process according to claim 13 wherein the polysaccharide concentration is in the range of from about 15 to about 35 wt. %.

15. A process according to claim 1 wherein for several oxidation cycles use is made of the same catalyst that is obtained after filtration of the reaction mixture and wherein, on conclusion of the reaction, the reaction mixture is heated at a temperature in the range of from about 50° C. to about 90° C.

* * * * *